(12) United States Patent
Kawamura et al.

(10) Patent No.: US 10,300,463 B2
(45) Date of Patent: May 28, 2019

(54) CATALYST FOR MANUFACTURING UNSATURATED ALDEHYDE AND/OR UNSATURATED CARBOXYLIC ACID AND MANUFACTURING METHOD OF SAME, AND MANUFACTURING METHOD OF UNSATURATED ALDEHYDE AND/OR UNSATURATED CARBOXYLIC ACID

(71) Applicant: NIPPON KAYAKU KABUSHIKI KAISHA, Tokyo (JP)

(72) Inventors: Tomoyuki Kawamura, Yamaguchi (JP); Motohiko Sugiyama, Yamaguchi (JP); Ryota Hiraoka, Yamaguchi (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/553,007

(22) PCT Filed: Feb. 25, 2016

(86) PCT No.: PCT/JP2016/055650
§ 371 (c)(1),
(2) Date: Aug. 23, 2017

(87) PCT Pub. No.: WO2016/136882
PCT Pub. Date: Sep. 1, 2016

(65) Prior Publication Data
US 2018/0029018 A1    Feb. 1, 2018

(30) Foreign Application Priority Data

Feb. 27, 2015 (JP) ................................. 2015-037574

(51) Int. Cl.
| | | |
|---|---|---|
| *C07C 45/35* | (2006.01) | |
| *C07C 45/27* | (2006.01) | |
| *C07C 51/25* | (2006.01) | |
| *C07C 51/16* | (2006.01) | |
| *B01J 23/887* | (2006.01) | |
| *B01J 23/00* | (2006.01) | |
| *B01J 37/08* | (2006.01) | |
| *B01J 37/00* | (2006.01) | |
| *C07B 61/00* | (2006.01) | |
| *B01J 37/04* | (2006.01) | |
| *B01J 35/08* | (2006.01) | |
| *B01J 37/02* | (2006.01) | |

(52) U.S. Cl.
CPC ......... *B01J 23/8872* (2013.01); *B01J 23/002* (2013.01); *B01J 23/887* (2013.01); *B01J 35/08* (2013.01); *B01J 37/0045* (2013.01); *B01J 37/0221* (2013.01); *B01J 37/04* (2013.01); *B01J 37/08* (2013.01); *C07C 45/27* (2013.01); *C07C 45/35* (2013.01); *C07C 51/16* (2013.01); *C07C 51/252* (2013.01); *C07B 61/00* (2013.01)

(58) Field of Classification Search
CPC ...... B01J 23/8876; B01J 23/88; B01J 23/002; C07C 45/35
See application file for complete search history.

(56) References Cited

U.S. PATENT DOCUMENTS

| | | | | |
|---|---|---|---|---|
| 4,792,620 | A | * 12/1988 | Paulik | .................. B01J 31/0231 560/232 |
| 5,929,275 | A | * 7/1999 | Wada | ..................... B01J 23/002 502/306 |
| 6,383,976 | B1 | 5/2002 | Arnold et al. | |
| 9,656,248 | B2 | * 5/2017 | Nakazawa | ........... B01J 37/0018 |
| 2005/0107641 | A1 | 5/2005 | Petzoldt et al. | |
| 2007/0142223 | A1 | 6/2007 | Petzoldt et al. | |
| 2013/0310604 | A1 | 11/2013 | Kurakami et al. | |
| 2016/0059218 | A1 | 3/2016 | Nakazawa et al. | |

FOREIGN PATENT DOCUMENTS

| | | | |
|---|---|---|---|
| CN | 102451710 | A | 5/2012 |
| CN | 102451710 | B * | 8/2013 |
| JP | 2003-146920 | A | 5/2003 |
| JP | 2003-164763 | A | 6/2003 |
| JP | 2007-511565 | T | 5/2007 |
| JP | 2008-149263 | A | 7/2008 |
| JP | 4683508 | B2 | 2/2011 |
| JP | 2012-115825 | A | 6/2012 |
| JP | 2012-176938 | A | 9/2012 |
| WO | 2014181839 | A1 | 11/2014 |

OTHER PUBLICATIONS

Norskov et al, Nature Chemistry, Towards the Computational Design of Solid Catalysts, 2009, 1, pp. 37-46. (Year: 2009).*
International Search Report from Patent Application No. PCT/JP2016/055650, dated Mar. 22, 2016.

* cited by examiner

*Primary Examiner* — Paul A Zucker
(74) *Attorney, Agent, or Firm* — Greenblum & Bernstein, P.L.C.

(57) ABSTRACT

Provided is a catalyst for manufacturing an unsaturated aldehyde and/or an unsaturated carboxylic acid, which is prepared by a method in which a molybdenum component raw material is composed of only an ammonium molybdate, the weight of water for dissolution is 8.5 times or less relative to the weight of molybdenum contained in the ammonium molybdate; and a bismuth component raw material is composed of only bismuth nitrate, the weight of a nitric acid aqueous solution for dissolution is 2.3 times or more relative to the weight of bismuth contained in the bismuth nitrate, and a nitric acid concentration in the nitric acid aqueous solution for dissolving the bismuth nitrate is 10% by weight or more.

3 Claims, 2 Drawing Sheets

CATALYST FOR MANUFACTURING UNSATURATED ALDEHYDE AND/OR UNSATURATED CARBOXYLIC ACID AND MANUFACTURING METHOD OF SAME, AND MANUFACTURING METHOD OF UNSATURATED ALDEHYDE AND/OR UNSATURATED CARBOXYLIC ACID

TECHNICAL FIELD

The present invention relates to a composite metal oxide catalyst that is used on the occasion of subjecting an alkene to gas-phase oxidation with molecular oxygen or a molecular oxygen-containing gas in the presence of an oxidation catalyst to manufacture a corresponding unsaturated aldehyde and/or unsaturated carboxylic acid and a manufacturing method of same, and a manufacturing method of an unsaturated aldehyde and/or an unsaturated carboxylic acid.

BACKGROUND ART

Production and manufacturing of catalysts for using an alkene as a raw material to manufacture a corresponding unsaturated aldehyde and unsaturated carboxylic acid are widely carried out on an industrial scale. Above all, there have hitherto been made a large number of proposals regarding catalysts for synthesis of acrolein and acrylic acid through gas-phase catalytic oxidation of propylene with molecular oxygen. Among them, a technology regarding atomic ratios of iron and cobalt and/or nickel is described in Patent Document 1, and it is described that by regulating the atomic ratio of iron to cobalt and/or nickel to a specified range, activity and selectivity can be improved. Patent Document 2 discloses a technology in which plural catalysts in which while making an atomic ratio of iron to an atomic ratios of cobalt and/or nickel constant, an atomic ratio of cobalt to the atomic ratio of cobalt and nickel is changed are prepared, and the catalysts are charged in two or more reaction zones within a reactor and used. Patent Document 3 discloses a technology regarding an annular unsupported catalyst in which an atomic ratio of cobalt to an atomic ratio of molybdenum and an atomic ratio of cobalt to an atomic ratio of iron are regulated to specified values, respectively. Patent Document 4 discloses a catalyst obtained by using bismuth trioxide or bismuth subcarbonate as a bismuth raw material and ultrasonically treating it. Patent Document 5 describes that in an oxide having specified atomic ratios and containing, as a main component a molybdate of cobalt and/or nickel and, as a secondary component, iron molybdate, activity and selectivity can be improved but is limitative such that molybdenum trioxide is not included in the oxide. In Patent Document 6, in addition to optimization of atomic ratios of respective elements to molybdenum, an atomic ratio of nickel to an atomic ratio of bismuth, an atomic ratio of nickel to an atomic ratio of an alkali metal component, and an atomic ratio of bismuth to an atomic ratio of an alkali metal component are investigated in detail, and effects thereof are clarified; however, any investigations of clarifying influences of the atomic ratios against the yield are not found.

BACKGROUND ART DOCUMENT

Patent Document

Patent Document 1: JP-A-2003-164763
Patent Document 2: JP-A-2003-146920
Patent Document 3: JP-T-2007-511565
Patent Document 4: JP-A-2008-149263
Patent Document 5: Japanese Patent No. 4683508
Patent Document 6: WO-A-2014/181839

SUMMARY OF INVENTION

Problem that Invention is to Solve

Even if the improvement is measured by the above-described means, a more improvement of the yield is demanded in subjecting an alkene to a partial oxidation reaction to manufacture a corresponding unsaturated aldehyde and/or unsaturated carboxylic acid. For example, the yield of the desired product affects the use amount of the alkene required for the manufacturing and significantly influences the manufacturing costs. In addition, since a large quantity of by-products is produced by continuing an operation at a low yield, a large load is given to the purification step, resulting in such a problem that time and operation costs taken in the purification step increase. Furthermore, there is a case where depending upon the kind of a by-product, such a by-product is accumulated on the catalyst surface or a gas passage in the vicinity of the catalyst. Since the accumulated by-product covers a necessary reaction active point of the catalyst surface to worsen the activity of the catalyst, the activity is needed to increase by force, and a reaction bath temperature must be increased. Then, the catalyst receives a thermal stress, and a lowering of the life or a reduction of the selectivity is caused, resulting in a decrease of the yield. In addition, it may also be considered that in view of the matter that an increase of the pressure within a system is caused due to a by-product accumulated within the system, the selectivity is reduced, resulting in a decrease of the yield. In the worst case, it may be even considered that a temperature anomaly is caused due to an abrupt increase of internal pressure, resulting in runaway of the reaction. If that is the case, it is also estimated that by stopping the operation over a long period of time, cleaning within the system or catalytic exchange becomes necessary. Then, an object of the present invention is to provide a catalyst in which an unsaturated aldehyde and/or an unsaturated carboxylic acid can be safely and inexpensively manufactured, and a yield of the desired product is high.

Means for Solving Problem

In order to solve the above-described problems, the present inventors made extensive and intensive investigations. As a result, it has been found that a composite metal oxide catalyst that is a catalyst composition satisfying specified atomic ratios, and in which in preparation of the catalyst, a molybdenum component raw material is an ammonium molybdate, a solvent for dissolving the ammonium molybdate is water; a bismuth component raw material is bismuth nitrate, a solvent for dissolving the bismuth nitrate is a nitric acid aqueous solution, with a weight of the water, a weight of the nitric acid aqueous solution, and an acid concentration of the nitric acid aqueous solution being satisfied with specified ranges, respectively; and the catalyst is prepared within a range where a composition ratio of bismuth to 12 of a molybdenum composition ratio is 0.4 or more and less than 0.8, is able to give a desired product at a high selectivity and a high yield, leading to accomplishment of the present invention.

That is, the present invention relates to:
(1) A catalyst for manufacturing an unsaturated aldehyde and/or an unsaturated carboxylic acid, comprising a compound represented by the following formula (1), the compound being prepared by a method in which in a step of preparing the compound represented by the following formula (1), a molybdenum component raw material is composed of only an ammonium molybdate, a weight of water for dissolution is 4.0 times or more and 8.5 times or less relative to a weight of molybdenum contained in the ammonium molybdate; and a bismuth component raw material is composed of only bismuth nitrate, a weight of a nitric acid aqueous solution for dissolution is 2.3 times or more relative to a weight of bismuth contained in the bismuth nitrate, and a nitric acid concentration in the nitric acid aqueous solution for dissolving the bismuth nitrate is 10% by weight or more:

$$Mo_{12}Bi_aFe_bCo_cNi_dX_eY_fZ_gO_h \qquad \text{Formula (1)}$$

wherein

X is at least one element selected from the group consisting of magnesium (Mg), calcium (Ca), manganese (Mn), copper (Cu), zinc (Zn), cerium (Ce), and samarium (Sm); Y is at least one element selected from the group consisting of boron (B), phosphorus (P), arsenic (As), antimony (Sb), and tungsten (W); Z is at least one element selected from the group consisting of sodium (Na), potassium (K), rubidium (Rb), and cesium (Cs); a to g represent atomic ratios of the respective components; h is a numerical value determined by oxidation degrees of the catalyst components; a=0.40 or more and less than 0.80; b=1.0 to 2.5; c=4.5 to 7.5; d=1.6 to 3.5; e=0 to 10; f=0 to 10; g=0.015 to 0.12; h is expressed by the numerical value satisfying the oxidation states of other elements; d/a is more than 2.0 and 8.8 or less; d/g is 14 or more and 100 or less; and a/g is 3.5 or more and less than 53.3;
(2) The catalyst for manufacturing an unsaturated aldehyde and/or an unsaturated carboxylic acid as described in (1),
wherein e and f in the formula (1) are 0;
(3) The catalyst for manufacturing an unsaturated aldehyde and/or an unsaturated carboxylic acid as described in (1) or (2),
wherein a preliminarily calcined powder obtained by calcining a dry powder that is obtained by drying a slurry containing the component represented by the formula (1) at a temperature of 200° C. or higher and 600° C. or lower; and again calcining the preliminarily calcined powder at a temperature of 200° C. or higher and 600° C. or lower;
(4) The catalyst for manufacturing an unsaturated aldehyde and/or an unsaturated carboxylic acid as described in any one of (1) to (3),
wherein the shaping method of the catalyst is a method of coating catalytically active components on a spherical carrier, an average particle diameter of the obtained catalyst is 3.0 mm to 10.0 mm, and a proportion of a weight of the catalytically active components occupying in the whole of the catalyst is 20 to 80% by weight;
(5) A method for manufacturing the catalyst for manufacturing an unsaturated aldehyde and/or an unsaturated carboxylic acid as described in any one of (1) to (4),
wherein in a step of preparing the compound represented by the formula (1), a molybdenum component raw material is composed of only an ammonium molybdate, a weight of water for dissolution is 4.0 times or more and 8.5 times or less relative to a weight of molybdenum contained in the ammonium molybdate; and a bismuth component raw material is composed of only bismuth nitrate, a weight of a nitric acid aqueous solution for dissolution is 2.3 times or more relative to a weight of bismuth contained in the bismuth nitrate, and a nitric acid concentration in the nitric acid aqueous solution for dissolving the bismuth nitrate is 10% by weight or more; and
(6) A method for manufacturing an unsaturated aldehyde and/or an unsaturated carboxylic acid, using the catalyst according to any one of (1) to (4).

Effects of Invention

In accordance with the present invention, a catalyst with high selectivity and yield of a desired product for manufacturing, from an alkene, a corresponding unsaturated aldehyde and/or unsaturated carboxylic acid can be obtained. According to this, it becomes possible to achieve a long-term operation safely and stably at a low cost.

MODE FOR CARRYING OUT INVENTION

Figure 1:
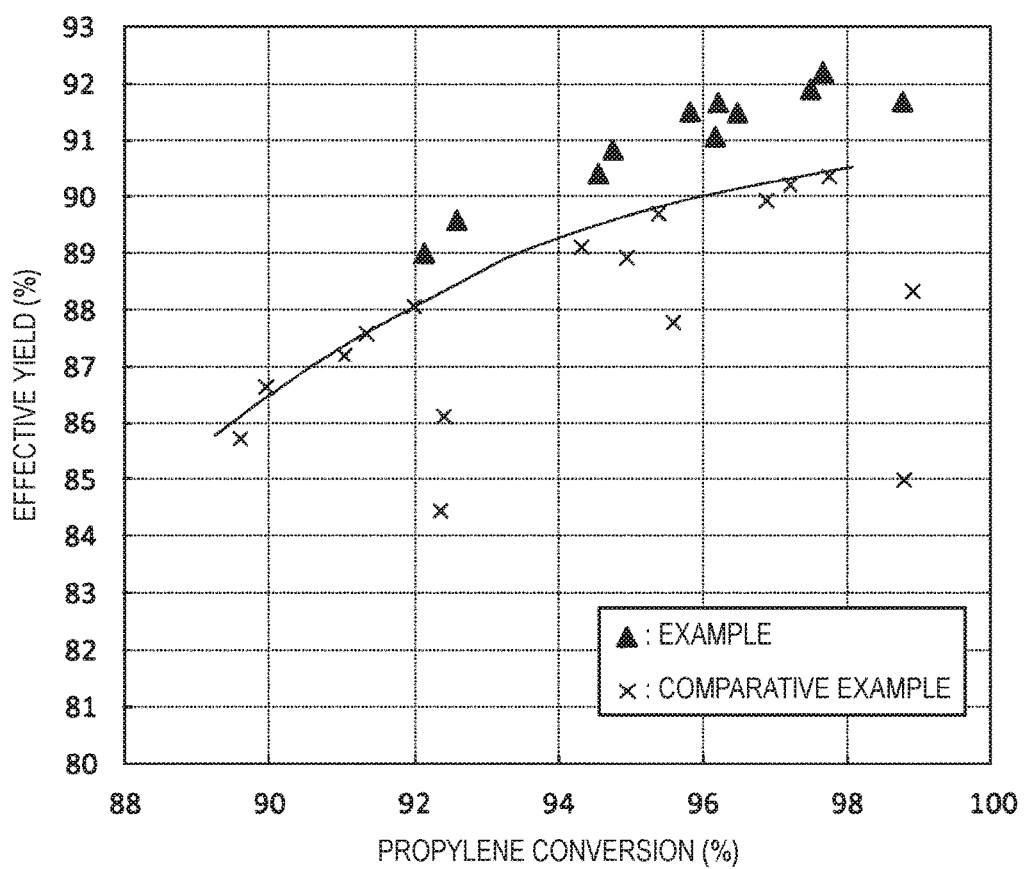
FIG. 1 is a graph showing an effective yield (%) relative to a propylene conversion (%) of each of catalysts in the Examples and Comparative Examples.

The catalyst of the present invention as represented by the following formula (1) can be prepared through the following steps.

$$Mo_{12}Bi_aFe_bCo_cNi_dX_eY_fZ_gO_n \qquad \text{Formula (1)}$$

In the formula, X is at least one element selected from the group consisting of magnesium (Mg), calcium (Ca), manganese (Mn), copper (Cu), zinc (Zn), cerium (Ce), and samarium (Sm); Y is at least one element selected from the group consisting of boron (B), phosphorus (P), arsenic (As), antimony (Sb), and tungsten (W); Z is at least one element selected from the group consisting of sodium (Na), potassium (K), rubidium (Rb), and cesium (Cs); a to g represent atomic ratios of the respective components; h is a numerical value determined by oxidation degrees of the catalyst components; a=0.40 or more and less than 0.80; b=1.0 to 2.5; c=4.5 to 7.5; d=1.6 to 3.5; e=0 to 10; f=0 to 10; g=0.015 to 0.12; h is expressed by the numerical value satisfying the oxidation states of other elements; d/a is more than 2.0 and 8.8 or less; d/g is 14 or more and 100 or less; and a/g is 3.5 or more and less than 53.3; and preferably a=0.45 or more and less than 0.75; b=1.5 to 2.4; c=4.7 to 7.0; d=1.8 to 3.2; e=0 to 10; f=0 to 10; g=0.02 to 0.11; h is expressed by the numerical value satisfying the oxidation states of other elements; d/a is more than 2.5 and 7.0 or less; d/g is 20 or more and 90 or less; and a/g is 5 or more and less than 25.
Step a) Preparation
In the present invention, as for starting raw materials of respective elements constituting the catalyst, in the case of using an ammonium molybdate as the molybdenum component raw material, a high-performance catalyst is obtained. In particular, the ammonium molybdate includes plural kinds of compounds, such as ammonium dimolybdate, ammonium tetramolybdate, ammonium heptamolybdate, etc., and among those, the case of using ammonium heptamolybdate is the most preferred. As for the bismuth component raw material, in the case of using bismuth nitrate, a high-performance catalyst is obtained. As for raw materials of iron, cobalt, nickel, and other elements, oxides, or nitrates, carbonates, organic acid salts, hydroxides, and the like, each of which may become an oxide upon ignition, or mixtures thereof can be generally used. For example, the iron component raw material and the cobalt component raw material and/or the nickel component raw material are dissolved in a desired ratio in water and mixed under a condition at 10 to 80° C.; the mixture is mixed with an aqueous solution or slurry of the separately prepared molybdenum component raw material and Z component raw material under a condition at 20 to 90° C.; after heating and stirring the resulting mixture for about 1 hour under a condition at 20 to 90° C. an aqueous solution having the bismuth component raw material dissolved therein, and optionally, the X component raw material and the Y component raw material are added, thereby obtaining an aqueous solution or slurry containing the catalyst components. The both are hereinafter collectively called "liquid preparation (A)".

Here, the liquid preparation (A) is not always required to contain all of the catalyst constituent elements, and a part of those elements or a part of the amounts thereof may be added in the sequent step or steps. In addition, on the occasion of preparing the liquid preparation (A), in the case of adding water in an amount for dissolving each of the component raw materials, or adding an acid, such as sulfuric acid, nitric acid, hydrochloric acid, tartaric acid, acetic acid, etc., a suitable viscosity of the liquid preparation (A) cannot be obtained unless the acid concentration in the aqueous solution sufficient for dissolving the raw materials is selected within a range of, for example, 5% by weight to 99% by weight, and such is not preferred from the standpoint of stable production. In particular, in dissolving the molybdenum component raw material, the molybdenum component raw material is composed of only an ammonium molybdate, the weight of water for dissolution is 4.0 times or more and 8.5 times or less relative to the weight of molybdenum contained in the ammonium molybdate; and in dissolving the bismuth component raw material, the bismuth component raw material is composed of only bismuth nitrate, the weight of the nitric acid aqueous solution for dissolution is 2.3 times or more relative to the weight of bismuth contained in the bismuth nitrate, and the nitric acid concentration in the nitric acid aqueous solution for dissolving the bismuth nitrate is 10% by weight or more. The form of the liquid preparation (A) thus obtained is preferably an aqueous solution or slurry from the standpoint that an excellent, catalyst is obtained. As for the amount of water for dissolving the ammonium molybdate, in the case where the weight of water for dissolution is less than 4.0 times relative to the weight of molybdenum contained in the ammonium molybdate, not only the ammonium molybdate is not sufficiently dissolved for forming a uniform slurry, but also the viscosity is too high, and hence, such is not preferred from the standpoint of manufacturing.

Here, as for the constituent element ratios, the ratio of bismuth that is one of the catalyst main components and the ratios of nickel and the alkali metal, each of which significantly affects the activity, are important. When d/a that is a ratio of nickel to bismuth is more than 2.0 and 8.8 or less, d/g that is a ratio of nickel to the alkali metal is 14 or more and 100 or less, and a/g that is a ratio of bismuth to the alkali metal is 3.5 or more and less than 53.3, an excellent catalyst with high selectivity and yield of the desired product is provided. In addition, by regulating the amount of bismuth to 0.40 or more and less than 0.80, and preferably 0.45 or more and less than 0.75, a higher yield is obtained. This effect does not reply upon a charging method. The effect may be, for example, obtained by single-layer filling. Taking into consideration reaction efficiency, a balance of temperature distribution, and the like, the effect is obtained through multilayer filling. In the multilayer filling, the effect is also obtained through a combination with a catalyst of other composition and filling. In addition, in either single-layer filling or multilayer filling, or in all of the layers, the treatment may also be made by mixing an inert substance and/or regulating the particle diameter as the need arises.

Step b) Drying

Subsequently, the liquid preparation (A) obtained above is dried to form a dry powder. The drying method is not particularly limited so long as it is a method capable of completely drying the liquid preparation (A); however, examples thereof include drum drying, freeze drying, spray drying, evaporation to dryness, and the like. Of these, spray drying in which the slurry can be dried into a powder or granule within a short period of time is especially preferred in the present invention. Although the drying temperature of spray drying varies depending upon the concentration of slurry, the liquid sending speed, or the like, it is approximately 70 to 150° C. in terms of a temperature at the outlet of a drying machine. In addition, it is preferred to perform drying such that an average particle diameter of the dry powder obtained on that occasion is 10 to 700 μm. There is thus obtained a dry powder (B).

Step c) Preliminary Calcination

When the obtained dry powder (B) is calcined under air circulation at 200° C. to 600° C., and preferably 300° C. to 600° C., shaping properties, mechanical strength, and catalytic performance of the resulting catalyst tend to be improved. A calcination time is preferably 1 hour to 12 hours. There is thus obtained a preliminarily calcined powder (C).

Step d) Shaping

Although the shaping method is not particularly limited, on the occasion of shaping in a cylindrical or annular form, a method using a tablet shaping machine, an extrusion shaping machine, or the like is preferred. The case of shaping in a spherical form is more preferred, and the preliminarily calcined powder (C) may be shaped in a spherical form by using a shaping machine; however, a method of supporting the preliminarily calcined powder (C) (including a shaping auxiliary agent and a strength improver, if desired) on a carrier, such as an inert ceramic, etc., is preferred. Here, as for the supporting method, a tumbling granulation method, a method using a centrifugal flow coating apparatus, a wash coating method, and the like are widely known, and the supporting method is not particularly limited so long as it is a method capable of uniformly supporting the preliminarily calcined powder (C) on the carrier. However, in the case of taking into account the manufacturing efficiency of the catalyst or the performance of the prepared catalyst, more preferably, a method in which using an apparatus having a flat or uneven disk in a bottom of a fixed cylindrical vessel, a carrier charged within the vessel is vigorously agitated by means of rotation motion and revolution motion of the disk itself by rotating the disk at a high speed, and the preliminarily calcined powder (C) and optionally a shaping auxiliary agent and/or a strength improver or a pore-forming agent are added thereto, thereby supporting the powder components on the carrier is preferred. It is to be noted that on the occasion of supporting, it is preferred to use a binder. Specific examples of the binder which may be used include water, ethanol, methanol, propanol, a polyhydric alcohol, polyvinyl alcohol of a polymer-based binder, a silica sol aqueous solution of an inorganic binder, and the like; ethanol, methanol, propanol, and a polyhydric alcohol are preferred; and a diol, such as ethylene glycol, etc., a triol, such as glycerin, etc., and the like are more preferred. By using an appropriate amount of a glycerin aqueous solution, the shaping properties become good, and a high-performance catalyst having high mechanical strength is obtained. Specifically, in the case of using an aqueous solution having a glycerin concentration of 5% by weight or more, a catalyst having an especially high performance is obtained. The use amount of such a binder is typically 2 to 80 parts by weight based on 100 parts by weight of the preliminarily calcined. powder (C). As for the inert carrier, a carrier having a diameter of about 2 to 8 mm is typically used, and the preliminarily calcined powder (C) is supported thereon. Its supporting rate is determined taking into account a catalyst use condition, for example, a reaction condition, such as a space velocity of the reaction raw materials, raw material concentrations, or the like, and it is typically 20% by weight to 80% by weight. Here, the supporting rate is expressed according to the following formula (3). There is thus obtained a shaped body (D). By drying the shaped body (D) prior to the full-scale calcination of the step e), a part of the used binder can also be evaporated.

Supporting rate (% by weight)=100×[(Weight of preliminarily calcined powder (C) used for shaping)/{(Weight of preliminarily calcined powder (C) used for shaping)+(Weight of inert carrier used for shaping)+(Weight of shaping assistant and strength improver used for shaping)}]  (3)

Step e) Full-Scale Calcination

By calcining the shaped body (D) at a temperature of 200 to 600° C. for about 1 to 12 hours, its catalytic activity and effective yield tend to be improved. The calcination temperature is preferably 400° C. or higher and 600° C. or lower, and more preferably 500° C. or higher and 600° C. or lower. Air is simple and easy and preferred as the gas to be circulated; however, besides, it is also possible to use nitrogen or carbon dioxide as an inert gas, or a nitrogen oxide-containing gas, an ammonia-containing gas, a hydrogen gas, or a mixture thereof for the purpose of rendering the system into a reducing atmosphere. There is thus obtained a catalyst (E). When the calcination temperature is made high, the activity can be properly controlled. Such a catalyst can be used, for example, on the raw material gas inlet side on which a hot spot is generated.

The catalytic gas-phase oxidation reaction of an alkene using the complex oxide catalyst obtained by the present invention can be carried out by introducing a mixed gas composed of 1 to 12% by volume of an alkene, 5 to 18% by volume of molecular oxygen, 0 to 60% by volume of steam, and 20 to 70% by volume of an inert gas, for example, nitrogen, carbon dioxide, etc., in terms of a raw material gas formulation onto the catalyst prepared above at a temperature ranging from 250 to 450° C. under a pressure of atmospheric pressure to 10 atms at a space velocity of 300 to 10,000 hr$^{-1}$. The alkene as referred to in the present invention also includes an alcohol capable of producing an alkene in its intramolecular dehydration reaction, for example, tertiary butanol.

The catalyst of the present invention can be used for manufacturing of an unsaturated aldehyde and/or an unsaturated carboxylic acid. Specifically, the catalyst of the present invention can be used for a method of subjecting propylene to gas-phase catalytic oxidation with molecular oxygen or a molecular oxygen-containing gas to manufacture acrolein and acrylic acid, or a method of subjecting isobutylene and/or tertiary butyl alcohol to gas-phase catalytic oxidation with molecular oxygen or a molecular oxygen-containing gas to manufacture methacrolein and methacrylic acid. Above all, it is preferred to use the catalyst of the present invention for manufacturing of acrolein and acrylic acid.

EXAMPLES

Examples are hereunder described by reference to specific examples, but it should be construed that the present invention is not limited to these Examples so long as the gist of the present invention is not deviated.

Example 1

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 30 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 715 mL of pure water warmed at 60° C. These solutions were gradually mixed while stirring. Thereafter, a solution prepared by adding 91.6 parts by weight of bismuth nitrate to a nitric acid aqueous solution (in a weight of 2.3 times the weight or more of bismuth in bismuth nitrate pentahydrate to be dissolved) which had been prepared by adding 23.3 parts by weight of nitric acid (60% by weight) to 97.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 530° C. for 4 hours, thereby obtaining Spherical Catalyst 1 having an average particle diameter of 5.2 mm according to the present invention. The catalyst calculated from the charged raw materials was found to be a composite metal oxide having the following atomic ratios.

The atomic ratios of the Spherical Catalyst 1 are d/a=6.0, d/g=37.5, and a/g=6.3. Mo:Bi:Fe:Co:Ni:K=12:0.50:2.0:6.5:3.0:0.08

Example 2

800 parts by weight of ammonium heptamolybdate tetrahydrate was completely dissolved in 3,040 parts by weight of pure water (in a weight of 7.0 times the weight of molybdenum) warmed at 60° C. Subsequently, 2.2 parts by weight of potassium nitrate was dissolved in 30 mL of pure water and added to the above-described solution. Subsequently, 259.3 parts by weight of ferric nitrate nonahydrate, 714.4 parts by weight of cobalt nitrate hexahydrate, and 263.5 parts by weight of nickel nitrate hexahydrate were dissolved in 655.7 mL of pure water warmed at 50° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 Mt of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 540° C. for 4 hours, thereby obtaining Spherical Catalyst 2 having an average particle diameter of 5.2 mm according to the present invention. The catalyst calculated from the charged raw materials was found to be a composite metal oxide having the following atomic ratios.

The atomic ratios of the Spherical Catalyst 2 are d/a=3.4, d/g=40, and a/g=12. Mo:Bi:Fe:Co:Ni:K=12:0.7:1.7: 6.5:2.4:0.06

Example 3

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 30 mL of pure water and added to the above-described solution. Subsequently 289.8 parts by weight of ferric nitrate nonahydrate, 692.4 parts by weight of cobalt nitrate hexahydrate, and 252.5 parts by weight of nickel nitrate hexahydrate were dissolved in 654.4 mL of pure water warmed at 60° C., These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 4'-0° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 530° C. for 4 hours, thereby obtaining Spherical Catalyst 3 having an average particle diameter of 5.2 mm according to the present invention. The catalyst calculated from the charged raw materials was found to be a composite metal oxide having the following atomic ratios.

The atomic ratios of the Spherical Catalyst 3 are d/a=3.3, d/g=29, and a/g=9. Mo:Bi:Fe:Co:Ni:K=12:0.7:1.9:6.3: 2.3:0.08

Example 4

800 parts by weight of ammonium heptamolybdate tetrahydrate was completely dissolved in 3,040 parts by weight of pure water (in a weight of 7.0 times the weight of molybdenum) warmed at 60° C. Subsequently, 1.1 parts by weight of rubidium nitrate was dissolved in 30 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 4 having an average particle diameter of 5.2 mm according to the present invention. The catalyst calculated from the charged raw materials was found to be a composite metal oxide having the following atomic ratios.

The atomic ratios of the Spherical Catalyst 4 are d/a=4.3, d/g=75, and a/g=18. Mo:Bi:Fe:Co:Ni:Rb=12:0.70:2.0: 6.5:3.0:0.04

Example 5

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of cesium nitrate was dissolved in 30 mL of pure water and added to the above-described solution. Subsequently, 305.1 parts by weight of ferric nitrate nonahydrate, 714.6 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 5 having an average particle diameter of 5.2 mm according to the present invention. The catalyst calculated from the charged raw materials was found to be a composite metal oxide, having the following atomic ratios.

The atomic ratios of the Spherical Catalyst 5 are d/a=4.3, d/g=75, and a/g=18. Mo:Bi:Fe:Co:Ni:Cs=12:0.7:2.0:6.5:3.0:0.04

Example 6

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 30 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 6 having an average particle diameter of 5.2 mm according to the present invention. The catalyst calculated from the charged raw materials was found to be a composite metal oxide having the following atomic ratios.

The atomic ratios of the Spherical Catalyst 6 are d/a=4.3, d/g=38, and a/g=9. Mo:Bi:Fe:Co:Ni:K=12:0.7:2.0:6.5:3.0:0.08

Example 7

800 parts by weight of ammonium heptamolybdate tetrahydrate was completely dissolved in 3,040 parts by weight of pure water (in a weight of 7.0 times the weight of molybdenum) warmed at 60° C. Subsequently, 1.4 parts by weight of potassium nitrate was dissolved in 30 mL of pure water and added to the above-described solution. Subsequently, 305.1 parts by weight of ferric nitrate nonahydrate, 714.4 parts by weight of cobalt nitrate hexahydrate, and 324.9 parts by weight of nickel nitrate hexahydrate were dissolved in 714.9 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 7 having an average particle diameter of 5.2 mm according to the present invention. The catalyst calculated from the charged raw materials was found to be a composite metal oxide having the following atomic ratios.

The atomic ratios of the Spherical Catalyst 7 are d/a=4.3, d/g=75, and a/g=18. Mo:Bi:Fe:Co:Ni:K=12:0.7:2.0:6.5:3.0:0.04

Example 8

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 30 mL, of pure water and added to the above-described solution. Subsequently, 259.3 parts by weight of ferric nitrate nonahydrate, 714.4 parts by weight of cobalt nitrate hexahydrate, and 263.5 parts by weight of nickel nitrate hexahydrate were dissolved in 655.7 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method.

Subsequently, calcination was carried out such that the resultant was held at a maximum temperature of 520° C. for 4 hours, thereby obtaining Spherical Catalyst 8 having an average particle diameter of 5.2 mm according to the present invention. The catalyst calculated from the charged raw materials was found to be a composite metal oxide having the following atomic ratios.

The atomic ratios of the Spherical Catalyst 8 are d/a=3.4, d/g=30, and a/g=9. Mo:Bi:Fe:Co:Ni:K=12:0.7:1.7:6.5: 2.4:0.08

Example 9

800 parts by weight of ammonium heptamolybdate tetrahydrate was completely dissolved in 3,040 parts by weight of pure water (in a weight of 7.0 times the weight of molybdenum) warmed at 60° C. Subsequently 3.7 parts by weight of potassium nitrate was dissolved in 30 of pure water and added to the above-described solution. Subsequently, 350.8 parts by weight of ferric nitrate nonahydrate, 538.5 parts by weight of cobalt nitrate hexahydrate, and 263.5 parts by weight of nickel nitrate hexahydrate were dissolved in 611.0 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 9 having an average particle diameter of 5.2 mm according to the present invention. The catalyst calculated from the charged raw materials was found to be a composite metal oxide having the following atomic ratios.

The atomic ratios of the Spherical Catalyst 9 are d/a=3.4, d/g=24, and a/g=7. Mo:Bi:Fe:Co:Ni:K=12:0.7:2.3:4.9: 2.4:0.1.

Example 10

800 parts by weight of ammonium heptamolybdate tetrahydrate was completely dissolved in 3,040 parts by weight of pure water (in a weight of 7.0 times the weight of molybdenum) warmed at 60° C. Subsequently, 3.7 parts by weight of potassium nitrate was dissolved in 42 mL of pure water and added to the above-described solution. Subsequently, 259.3 parts by weight of ferric nitrate nonahydrate, 714.4 parts by weight of cobalt nitrate hexahydrate, and 324.9 parts by weight of nickel nitrate hexahydrate were dissolved in 690.6 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 10 having an average particle diameter of 5.2 mm according to the present invention. The catalyst calculated from the charged raw materials was found to be a composite metal oxide having the following atomic ratios.

The atomic ratios of the Spherical Catalyst 10 are d/a=4.3, d/g=30, and a/g=7. Mo:Bi:Fe:Co:Ni:K=12:0.7:1.7:6.5: 3.0:0.1

Example 11

800 parts by weight of ammonium heptamolybdate tetrahydrate was completely dissolved in 3,040 parts by weight of pure water (in a weight of 7.0 times the weight of molybdenum) warmed at 60° C. Subsequently, 3.7 parts by weight of potassium nitrate was dissolved in 42 mL of pure water and added to the above-described solution. Subsequently, 350.8 parts by weight of ferric nitrate nonahydrate, 549.5 parts by weight of cobalt nitrate hexahydrate, and 263.5 parts by weight of nickel nitrate hexahydrate were dissolved in 616.8 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently calcination was carried out such that the resultant was held at a maximum temperature of 520° C. for 4 hours, thereby obtaining Spherical Catalyst 11 having an average particle diameter of 5.2 mm according to the present invention. The catalyst calculated from the charged raw materials was found to be a composite metal oxide having the following atomic ratios.

The atomic ratios of the Spherical Catalyst 11 are d/a=3.4, d/g=24, and a/g=7. Mo:Bi:Fe:Co:Ni:K=12:0.7:2.3:5.0: 2.4:0.1.

Comparative Example 1

800 parts by weight of ammonium heptamolybdate tetrahydrate was completely dissolved in 3,040 parts by weight of pure water (in a weight of 7.0 times the weight of molybdenum) warmed at 60° C. Subsequently, 3.7 parts by weight of potassium nitrate was dissolved in 42 mL of pure water and added to the above-described solution. Subsequently, 274.6 parts by weight of ferric nitrate nonahydrate, 571.5 parts by weight of cobalt nitrate hexahydrate, and 307.4 parts by weight of nickel nitrate hexahydrate were dissolved in 611.4 mL of pure water warmed at 60° C. These solutions were gradually mixed while stirring. Thereafter, a solution prepared by adding 311.4 parts by weight of bismuth nitrate to a nitric acid aqueous solution (in a weight of 2.3 times the weight or more of bismuth in bismuth nitrate pentahydrate to be dissolved) which had been prepared by adding 79.3 parts by weight of nitric acid (60% by weight) to 330.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 550° C. for 4 hours, thereby obtaining Spherical Catalyst 12 having an average particle diameter of 5.2 mm for comparison. The catalyst calculated from the charged raw materials was found to be a composite metal oxide having the following atomic ratios.

The atomic ratios of the Spherical Catalyst 12 are $d/a=1.6$, $d/g=28$, and $a/g=17$. Mo:Bi:Fe:Co:Ni:K=12:1.7:1.8: 5.2:2.8:0.1

Comparative Example 2

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of cesium nitrate was dissolved in 30 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warned at 60° C. These solutions were gradually mixed while stirring. Thereafter, a solution prepared by adding 164.8 parts by weight of bismuth nitrate to a nitric acid aqueous solution a weight of 2.3 times the weight or more of bismuth in bismuth nitrate pentahydrate to be dissolved) which had been prepared by adding 42.0 parts by weight of nitric acid (60% by weight) to 174.7 of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 540° C. for 4 hours, thereby obtaining Spherical Catalyst 13 having an average particle diameter of 5.2 mm for comparison. The catalyst calculated from the charged raw materials was found to be a composite metal oxide having the following atomic ratios.

The atomic ratios of the Spherical Catalyst 13 are $d/a=3.3$, $d/g=75$, and $a/g=23$. Mo:Bi:Fe:Co:Ni:Cs=12:0.9:2.0: 6.5:3.0:0.04

Comparative Example 3

800 parts by weight of ammonium heptamolybdate tetrahydrate was completely dissolved in 3,040 parts by weight of pure water (in a weight of 7.0 times the weight of molybdenum) warmed at 60° C. Subsequently, 1.0 part by weight of potassium nitrate was dissolved in 30 mL of pure water and added to the above-described solution. Subsequently, 259.3 parts by weight of ferric nitrate nonahydrate, 769.4 parts by weight of cobalt nitrate hexahydrate, and 219.6 parts by weight of nickel nitrate hexahydrate were dissolved in 661.6 of pure water warmed at 60° C. These solutions were gradually mixed while stirring. Thereafter, a solution prepared by adding 183.2 parts by weight of bismuth nitrate to a nitric acid aqueous solution (in a weight of 2.3 times the weight or more of bismuth in bismuth nitrate pentahydrate to be dissolved) which had been prepared by adding 46.6 parts by weight of nitric acid (60% by weight) to 194.2 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 540° C. for 4 hours, thereby obtaining Spherical Catalyst 14 having an average particle diameter of 5.2 mm for comparison. The catalyst calculated from the charged raw materials was found to be a composite metal oxide having the following atomic ratios.

The atomic ratios of the Spherical Catalyst 14 are $d/a=2$, $d/g=67$, and $a/g=33$. Mo:Bi:Fe:Co:Ni:K=12:1.0:1.7: 7.0:2.0:0.03

Comparative Example 4

800 parts by weight of ammonium heptamolybdate tetrahydrate was completely dissolved in 3,040 parts by weight of pure water (in a weight of 7.0 times the weight of molybdenum) warmed at 60° C., Subsequently, 19.0 parts by weight of potassium nitrate was dissolved in 200 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 91.6 parts by weight of bismuth nitrate to a nitric acid aqueous solution (in a weight of 2.3 times the weight or more of bismuth in bismuth nitrate pentahydrate to be dissolved) which had been prepared by adding 23.3 parts by weight of nitric acid (60% by weight) to 97.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 15 having an average particle diameter of 5.2 mm for comparison. The catalyst calculated from the charged raw materials was found to be a composite metal oxide having the following atomic ratios.

The atomic ratios of the Spherical Catalyst 15 are d/a=6.0, d/g=6, and a/g=1. Mo:Bi:Fe:Co:Ni:K=12:0.5:2.0:6.5:3.0:0.5

Comparative Example 5

800 parts by weight of ammonium heptamolybdate tetrahydrate was completely dissolved in 3,040 parts by weight of pure water (in a weight of 7.0 times the weight of molybdenum) warmed at 60° C. Subsequently, 1.5 parts by weight of cesium nitrate was dissolved in 200 mL of pure water and added to the above-described solution. Subsequently, 259.3 parts by weight of ferric nitrate nonahydrate, 714.4 parts by weight of cobalt nitrate hexahydrate, and 263.5 parts by weight of nickel nitrate hexahydrate were dissolved in 680.0 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 23.3 parts by weight of nitric acid (60% by weight) to 97.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical limn in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 16 having an average particle diameter of 5.2 mm for comparison. The catalyst calculated from the charged raw materials was found to be a composite metal oxide having the following atomic ratios.

The atomic ratios of the Spherical Catalyst 16 are d/a=3.4, d/g=120, and a/g=35. Mo:Bi:Fe:Co:Ni:Cs=12:0.7:1.7:6.5:2.4:0.02

Comparative Example 6

800 parts by weight of ammonium heptamolybdate tetrahydrate was completely dissolved in 3,040 parts by weight of pure water (in a weight of 7.0 times the weight of molybdenum) warmed at 60° C. Subsequently, 7.5 parts by weight of potassium nitrate was dissolved in 200 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 17 having an average particle diameter of 5.2 mm for comparison. The catalyst calculated from the charged raw materials was found to be a composite metal oxide having the following atomic ratios.

The atomic ratios of the Spherical Catalyst 17 are d/a=4.3, d/g=15, and a/g=4. Mo:Bi:Fe:Co:Ni:K=12:0.7:2.0:6.5:3.0:0.2

Comparative Example 7

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 100 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 155.7 parts by weight of bismuth nitrate to a nitric acid aqueous solution (in a weight of 2.3 times the weight or more of bismuth in bismuth nitrate pentahydrate to be dissolved) which had been prepared by adding 39.6 parts by weight of nitric acid (60% by weight) to 165.0 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 18 having an average particle diameter of 5.2 mm for comparison. The catalyst calculated from the charged raw materials was found to be a composite metal oxide having the following atomic ratios.

The atomic ratios of the Spherical Catalyst 18 are d/a=3.3, d/g=38, and a/g 11. Mo:Bi:Fe:Co:Ni:K=12:0.9:2.0:6.5:3.0:0.08

Comparative Example 8

800 parts by weight of ammonium heptamolybdate tetrahydrate was completely dissolved in 3.040 parts by weight of pure water (in a weight of 7.0 (a times the weight of molybdenum) warmed at 60° C. Subsequently, 2.9 parts by weight of potassium nitrate was dissolved in 100 mL of pure water and added to the above-described solution. Subsequently, 305.1 parts by weight of ferric nitrate nonahydrate, 714.4 parts by weight of cobalt nitrate hexahydrate, and 263.5 parts by weight of nickel nitrate hexahydrate were dissolved in 680.0 mL of pure water warmed at 60° C. These solutions were gradually mixed while stirring. Thereafter, a solution prepared by adding 228.9 parts by weight of bismuth nitrate to a nitric acid aqueous solution (in a weight of 2.3 times the weight or more of bismuth in bismuth nitrate pentahydrate to be dissolved) which had been prepared by adding 58.3 parts by weight of nitric acid (60% by weight) to 242.7 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 19 having an average particle diameter of 5.2 rum for comparison. The catalyst calculated from the charged raw materials was found to be a composite metal oxide having the following atomic ratios.

The atomic ratios of the Spherical Catalyst 19 are d/a=1.8, d/g=30, and a/g=16. Mo:Bi:Fe:Co:Ni:K=12:1.3:2.0:6.5:2.4:0.08

Comparative Example 9

800 parts by weight of ammonium heptamolybdate tetrahydrate was completely dissolved in 3,040 parts by weight of pure water (in a weight of 7.0 times the weight of molybdenum) warmed at 60° C. Subsequently, 1.8 parts by weight of potassium nitrate was dissolved in 100 mL of pure water and added to the above-described solution. Subsequently, 149.5 parts by weight of ferric nitrate nonahydrate, 714.4 parts by weight of cobalt nitrate hexahydrate, and 263.5 parts by weight of nickel nitrate hexahydrate were dissolved in 680.0 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 20 having an average particle diameter of 5.2 mm for comparison. The catalyst calculated from the charged raw materials was found to be a composite metal oxide having the following atomic ratios.

The atomic ratios of the Spherical Catalyst 20 are d/a=3.4, d/g=48, and a/g=14. Mo:Bi:Fe:Co:Ni:K=12:0.7:0.9:6.5:2.4:0.05

Comparative Example 10

800 parts by weight of ammonium heptamolybdate tetrahydrate was completely dissolved in 3,040 parts by weight of pure water (in a weight of 7.0 times the weight of molybdenum) warmed at 60° C. Subsequently, 1.4 parts by weight of potassium nitrate was dissolved in 100 mL of pure water and added to the above-described solution. Subsequently, 228.8 parts by weight of ferric nitrate nonahydrate, 769.4 parts by weight of cobalt nitrate hexahydrate, and 131.8 parts by weight of nickel nitrate hexahydrate were dissolved in 598.9 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 21 having an average particle diameter of 5.2 mm for comparison. The catalyst calculated from the charged raw materials was found to be a composite metal oxide having the following atomic ratios.

The atomic ratios of the Spherical Catalyst 21 are d/a=1.7, d/g=30, and a/g=18. Mo:Bi:Fe:Co:Ni:K=12:0.7:1.5:7.0:1.2:0.04

Comparative Example 11

800 parts by weight of ammonium heptamolybdate tetrahydrate was completely dissolved in 3,040 parts by weight of pure water (in a weight of 7.0 times the weight of molybdenum) warmed at 60° C. Subsequently, 1.4 parts by weight of potassium nitrate was dissolved in 100 mL of pure water and added to the above-described solution. Subsequently, 442.4 parts by weight of ferric nitrate nonahydrate, 714.4 parts by weight of cobalt nitrate hexahydrate, and 329.4 parts by weight of nickel nitrate hexahydrate were dissolved in 787.7 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 22 having an average particle diameter of 5.2 mm for comparison. The catalyst calculated from the charged raw materials was found to be a composite metal oxide having the following atomic ratios.

The atomic ratios of the Spherical Catalyst 22 are d/a=4.3, d/g=75, and a/g=18. Mo:Bi:Fe:Co:Ni:K=12:0.7:2.9:6.5:3.0:0.04

Comparative Example 12

800 parts by weight of ammonium heptamolybdate tetrahydrate was completely dissolved in 3,040 parts by weight of pure water (in a weight of 7.0 times the weight of molybdenum) warmed at 60° C. Subsequently, 5.6 parts by weight of potassium nitrate was dissolved in 65 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 91.6 parts by weight of bismuth nitrate to a nitric acid aqueous solution (in a weight of 2.3 times the weight or more of bismuth in bismuth nitrate pentahydrate to be dissolved) which had been prepared by adding 23.3 parts by weight of nitric acid (60% by weight) to 97.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 23 having an average particle diameter of 5.2 mm for comparison. The catalyst calculated from the charged raw materials was found to be a composite metal oxide having the following atomic ratios.

The atomic ratios of the Spherical Catalyst 23 are d/a=6, d/g=20, and a/g=3. Mo:Bi:Fe:Co:Ni:K=12:0.5:2.0:6.5:3.0:0.15

Comparative Example 13

800 parts by weight of ammonium heptamolybdate tetrahydrate was completely dissolved in 3,040 parts by weight of pure water (in a weight of 7.0 times the weight of molybdenum) warmed at 60° C. Subsequently, 7.5 parts by weight of potassium nitrate was dissolved in 85 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 91.6 parts by weight of bismuth nitrate to a nitric acid aqueous solution (in a weight of 2.3 times the weight or more of bismuth in bismuth nitrate pentahydrate to be dissolved) which had been prepared by adding 23.3 parts by weight of nitric acid (60% by weight) to 97.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 2.4 having an average particle diameter of 5.2 mm for comparison. The catalyst calculated from the charged raw materials was found to be a composite metal oxide having the following atomic ratios.

The atomic ratios of the Spherical Catalyst 24 are d/a=6, d/g=15, and a/g=2.5. Mo:Bi:Fe:Co:Ni:K=12:0.5:2.0:6.5:3.0:0.20

Comparative Example 14

800 parts by weight of ammonium heptamolybdate tetrahydrate was completely dissolved in 3,040 parts by weight of pure water (in a weight of 7.0 times the weight of molybdenum) warmed at 60° C., Subsequently, 5.6 parts by weight of potassium nitrate was dissolved in 65 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 680.0 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slim was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 25 having an average particle diameter of 5.2 mm for comparison. The catalyst calculated from the charged raw materials was found to be a composite metal oxide having the following atomic ratios.

The atomic ratios of the Spherical Catalyst 25 are d/a=4.3, d/g=20, and a/g=5. Mo:Bi:Fe:Co:Ni:K=12:0.7:2.0:6.5: 3.0:0.15

Comparative Example 15

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 30 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 54.9 parts by weight of bismuth nitrate to a nitric acid aqueous solution (in a weight of 2.3 times the weight or more of bismuth in bismuth nitrate pentahydrate to be dissolved) which had been prepared by adding 14.0 parts by weight of nitric acid (60% by weight) to 58.2 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 26 having an average particle diameter of 5.2 mm for comparison. The catalyst calculated from the charged raw materials was found to be a composite metal oxide having the following atomic ratios.

The atomic ratios of the Spherical Catalyst 26 are d/a=10, d/g=38, and a/g=4. Mo:Bi:Fe:Co:Ni:K=12:0.3:2.0:6.5: 3.0:0.08

Comparative Example 16

800 parts by weight of ammonium heptamolybdate tetrahydrate was completely dissolved in 3,040 parts by weight of pure water (in a weight of 7.0 times the weight of molybdenum) warmed at 60° C. Subsequently, 1.2 parts by weight of potassium nitrate was dissolved in 100 mL of pure water and added to the above-described solution. Subsequently, 305.1 parts by weight of ferric nitrate nonahydrate, 714.4 parts by weight of cobalt nitrate hexahydrate, and 439.2 parts by weight of nickel nitrate hexahydrate were dissolved in 773.1 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 27 having an average particle diameter of 5.2 mm for comparison. The catalyst calculated from the charged raw materials was found to be a composite metal oxide having the following atomic ratios.

The atomic ratios of the Spherical Catalyst 27 are d/a=5.7, d/g=114, and a/g=20. Mo:Bi:Fe:Co:Ni:K=12:0.7:2.0: 6.5:4.0:0.035

Comparative Example 17

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 100 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 91.6 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 9% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 28 having an average particle diameter of 5.2 mm for comparison. The catalyst calculated from the charged raw materials was found to be a composite metal oxide having the following atomic ratios.

The atomic ratios of the Spherical Catalyst 28 are d/a=6, d/g=38, and a/g=6. Mo:Bi:Fe:Co:Ni:K=12:0.5:2.0:6.5:3.0:0.08

Though the Catalyst 28 was obtained by changing the nitric acid concentration in Example 1, the activity was significantly lowered as compared with that in Example 1.

Comparative Example 18

800 parts by weight of ammonium heptamolybdate tetrahydrate was completely dissolved in 3,040 parts by weight of pure water (in a weight of 7.0 times the weight of molybdenum) warmed at 60° C. Subsequently, 2.9 parts by weight of potassium nitrate was dissolved in 100 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 714.9 mL of pure water warmed at 60° C. These solutions were gradually mixed while stirring. Thereafter, a solution prepared by adding 91.6 parts by weight of bismuth nitrate to a nitric acid aqueous solution (in a weight of 2 times the weight or more of bismuth in bismuth nitrate pentahydrate to be dissolved) which had been prepared by adding 15.8 parts by weight of nitric acid (60% by weight) to 63.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 29 having an average particle diameter of 5.2 mm for comparison. The catalyst calculated from the charged raw materials was found to be a composite metal oxide having the following atomic ratios.

The atomic ratios of the Spherical Catalyst 29 are d/a=6, d/g=38, and a/g=6. Mo:Bi:Fe:Co:Ni:K=12:0.5:2.0:6.5:3.0:0.08

Though the Catalyst 29 was obtained by changing the weight of the nitric acid solution in Example 1, the activity was significantly lowered as compared with that in Example 1.

Comparative Example 19

800 parts by weight of ammonium heptamolybdate tetrahydrate was completely dissolved in 3,912 parts by weight of pure water (in a weight of 9.0 times the weight of molybdenum) warmed at 60° C. Subsequently, 2.9 parts by weight of potassium nitrate was dissolved in 100 mL of pure water and added to the above-described solution. Subsequently, 305.1 parts by weight of ferric nitrate nonahydrate, 714.4 parts by weight of cobalt nitrate hexahydrate, and 329.4 parts by weight of nickel nitrate hexahydrate were dissolved in 680.0 mL of pure water warmed at 60° C. These solutions were gradually mixed while stirring. Thereafter, a solution prepared by adding 91.6 parts by weight of bismuth nitrate to a nitric acid aqueous solution (in a weight of 2.3 times the weight or more of bismuth in bismuth nitrate pentahydrate to be dissolved) which had been prepared by adding 23.3 parts by weight of nitric acid (60% by weight) to 97.1 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 30 having an average particle diameter of 5.2 mm for comparison. The catalyst calculated from the charged raw materials was found to be a composite metal oxide having the following atomic ratios.

The atomic ratios of the Spherical Catalyst 30 are d/a=6, d/g=38, and a/g=6. Mo:Bi:Fe:Co:Ni:K=12:0.5:2.0:6.5:3.0:0.08

Though the Catalyst 30 was obtained by changing the amount of water for dissolving the ammonium molybdate in Example 1, the activity was significantly lowered as compared with that in Example 1.

Comparative Example 20

800 parts by weight of ammonium heptamolybdate tetrahydrate was completely dissolved in 3,040 parts by weight of pure water (in a weight of 7.0 times the weight of molybdenum) warmed at 60° C., Subsequently, 0.2 parts by weight of potassium nitrate was dissolved in 100 mL of pure water and added to the above-described solution. Subsequently, 305.1 parts by weight of ferric nitrate nonahydrate, 714.4 pans by weight of cobalt nitrate hexahydrate, and 219.6 parts by weight of nickel nitrate hexahydrate were dissolved in 680.0 mL of pure water warmed at 60° C., These solutions were gradually mixed while stirring. Thereafter, a solution prepared by adding 73.3 parts by weight of bismuth nitrate to a nitric acid aqueous solution (in a weight of 2.3 times the weight or more of bismuth in bismuth nitrate pentahydrate to be dissolved) which had been prepared by adding 18.7 parts by weight of nitric acid (60% by weight) to 77.7 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 31 having an average particle diameter of 5.2 mm for comparison. The catalyst calculated from the charged raw materials was found to be a composite metal oxide having the following atomic ratios.

The atomic ratios of the Spherical Catalyst 31 are d/a=5, d/g=200, and a/g=40. Mo:Bi:Fe:Co:Ni:K=12:0.4:2.0: 6.5:2.0:0.01

Comparative Example 21

800 parts by weight of ammonium heptamolybdate tetrahydrate was completely dissolved in 3,040 parts by weight of pure water (in a weight of 77.0 times the weight of molybdenum) warmed at 60° C. Subsequently, 1.4 parts by weight of potassium nitrate was dissolved in 100 mL of pure water and added to the above-described solution. Subsequently, 305.1 pans by weight of ferric nitrate nonahydrate, 901.2 parts by weight of cobalt nitrate hexahydrate, and 263.5 parts by weight of nickel nitrate hexahydrate were dissolved in 779.0 of pure water warmed at 60° C. These solutions were gradually mixed while stirring. Thereafter, a solution prepared by adding 164.8 parts by weight of bismuth nitrate to a nitric acid aqueous solution (in a weight of 2.3 times the weight or more of bismuth in bismuth nitrate pentahydrate to be dissolved) which had been prepared by adding 42 parts by weight of nitric acid (60% by weight) to 174.7 of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 32 having an average particle diameter of 5.2 mm for comparison. The catalyst calculated from the charged raw materials was found to be a composite metal oxide having the following atomic ratios.

The atomic ratios of the Spherical Catalyst 32 are d/a=2.7, d/g=60, and a/g=40. Mo:Bi:Fe:Co:M:K=12:0.9:2.0: 8.2:2.4:0.04

Comparative Example 22

800 parts by weight of ammonium heptamolybdate tetrahydrate was completely dissolved in 3,040 parts by weight of pure water (in a weight of 7.0 times the weight of molybdenum) warmed at 60° C. Subsequently, 1.4 parts by weight of potassium nitrate was dissolved in 30 mL of pure water and added to the above-described solution. Subsequently, 305.1 parts by weight of ferric nitrate nonahydrate, 439.6 parts by weight of cobalt nitrate hexahydrate, and 329.4 parts by weight of nickel nitrate hexahydrate were dissolved in 569.3 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed. Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 33 having an average particle diameter of 5.2 mm for comparison. The catalyst calculated from the charged raw materials was found to be a composite metal oxide having the following atomic ratios.

The atomic ratios of the Spherical Catalyst 33 are d/a=4.3, d/g=75, and a/g=18. Mo:Bi:Fe:Co:Ni:K=12:0.7:2.0: 4.0:3.0:0.04

Comparative Example 23

800 parts by weight of ammonium heptamolybdate tetrahydrate was completely dissolved in 3,040 parts by weight of pure water (in a weight of 7.0 times the weight of molybdenum) warmed at 60° C. Subsequently, 1.4 parts by weight of potassium nitrate was dissolved in 100 mL of pure water and added to the above-described solution. Subsequently, 305.1 parts by weight of ferric nitrate nonahydrate, 879.3 parts by weight of cobalt nitrate hexahydrate, and 324.9 parts by weight of nickel nitrate hexahydrate were dissolved in 802.3 mL of pure water warmed at 60° C. These solutions were gradually mixed while stirring. Thereafter, a solution prepared by adding 128.2 parts by weight of bismuth nitrate to a nitric acid aqueous solution (in a weight of 2.3 times the weight or more of bismuth in bismuth nitrate pentahydrate to be dissolved) which had been prepared by adding 32.6 parts by weight of nitric acid (60% by weight) to 135.9 mL of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 4 hours. Crystalline cellulose was added in a proportion of 5% by weight relative to the preliminarily calcined powder and thoroughly mixed.

Thereafter, the mixture was supported and shaped in a spherical form in a supporting rate of 50% by weight on an inert spherical carrier by using a 30% by weight glycerin solution as a binder by a tumbling granulation method. Subsequently, calcination was carried out such that the resultant was held at a maximum temperature of 520° C. for 4 hours, thereby obtaining Spherical Catalyst 34 having an average particle diameter of 5.2 mm for comparison. The catalyst calculated from the charged raw materials was found to be a composite metal oxide having the following atomic ratios.

The atomic ratios of the Spherical Catalyst 34 are d/a=4.3, d/g=75, and a/g=18. Mo:Bi:Fe:Co:Ni:K=12:0.7:2.0:8.0:3.0:0.04

The results of the oxidation reaction of propylene are hereunder shown. Here, the definitions of propylene conversion, acrolein yield, acyclic acid yield, and effective yield are as follows.

Propylene conversion (mol %) = {(Molar number of reacted propylene)/(Molar number of fed propylene)} × 100

Acrolein yield (mol %) = {(Molar number of produced acrolein)/(Molar number of fed propylene)} × 100

Acrylic acid yield (mol %) = {(Molar number of produced acrylic acid)/(Molar number of fed propylene)} × 100

Effective yield (mol %) = {(Acrolein yield) + (Acrylic acid yield)}

(Reaction Condition)

Using each of the thus-prepared Spherical Catalysts 1 to 34, the oxidation reaction of propylene was carried out to determine the propylene conversion, the acrolein yield, the acrylic acid yield, and the effective yield. 67.7 mL of the catalyst was charged in a stainless steel-made reaction tube having an inside diameter of 28.4 mm, a mixed gas of 8% by volume of propylene, 67% by volume of air, and 25% by volume of steam was introduced at a space velocity of about 860 hr$^{-1}$ to carry out the oxidation reaction of propylene, and the reaction bath temperature and the propylene conversion at which the effective yield became maximum were determined and shown in Table 1.

TABLE 1

| | a | b | c | d | g | d/a | d/g | a/g | Reaction bath temperature (° C.) | Propylene conversion (%) | Effective yield (%) |
|---|---|---|---|---|---|---|---|---|---|---|---|
| Example 1 | 0.5 | 2.0 | 6.5 | 3.0 | 0.08 | 6.0 | 38 | 6 | 340 | 96.50 | 91.50 |
| Example 2 | 0.7 | 1.7 | 6.5 | 3.4 | 0.06 | 3.4 | 40 | 12 | 330 | 95.84 | 91.52 |
| Example 3 | 0.7 | 1.9 | 6.3 | 2.3 | 0.08 | 3.3 | 29 | 9 | 350 | 92.60 | 89.60 |
| Example 4 | 0.7 | 2.0 | 6.5 | 3.0 | 0.04 | 4.3 | 75 | 18 | 320 | 98.78 | 91.70 |
| Example 5 | 0.7 | 2.0 | 6.5 | 3.0 | 0.04 | 4.3 | 75 | 18 | 350 | 96.19 | 91.08 |
| Example 6 | 0.7 | 2.0 | 6.5 | 3.0 | 0.08 | 4.3 | 38 | 9 | 310 | 97.52 | 91.92 |
| Example 7 | 0.7 | 2.0 | 6.5 | 3.0 | 0.04 | 4.3 | 75 | 18 | 310 | 97.69 | 92.23 |
| Example 8 | 0.7 | 1.7 | 6.5 | 2.4 | 0.08 | 3.4 | 30 | 9 | 330 | 94.77 | 90.85 |
| Example 9 | 0.7 | 2.3 | 4.9 | 2.4 | 0.1 | 3.4 | 24 | 7 | 350 | 92.15 | 89.02 |
| Example 10 | 0.7 | 1.7 | 6.5 | 3.0 | 0.1 | 4.3 | 30 | 7 | 310 | 96.23 | 91.68 |
| Example 11 | 0.7 | 2.3 | 5.0 | 2.4 | 0.1 | 3.4 | 24 | 7 | 330 | 94.57 | 90.43 |
| Comparative Example 1 | 1.7 | 1.8 | 5.2 | 2.8 | 0.1 | 1.6 | 28 | 17 | 330 | 91.05 | 87.21 |
| Comparative Example 2 | 0.9 | 2.0 | 6.5 | 3.0 | 0.01 | 3.3 | 75 | 13 | 330 | 91.35 | 87.60 |
| Comparative Example 3 | 1.0 | 1.7 | 7.0 | 2.0 | 0.03 | 2.0 | 67 | 33 | 310 | 98.91 | 88.35 |
| Comparative Example 4 | 0.5 | 2.0 | 6.5 | 3.0 | 0.5 | 6.0 | 6 | 1 | 350 | 92.36 | 84.46 |
| Comparative Example 5 | 0.7 | 1.7 | 6.5 | 2.4 | 0.02 | 3.4 | 120 | 35 | 320 | 92.41 | 86.13 |
| Comparative Example 6 | 0.7 | 2.0 | 6.5 | 3.0 | 0.2 | 4.3 | 15 | 4 | 320 | 97.23 | 90.23 |
| Comparative Example 7 | 0.9 | 2.0 | 6.5 | 3.0 | 0.08 | 3.3 | 38 | 11 | 310 | 96.89 | 89.95 |
| Comparative Example 8 | 1.3 | 2.0 | 6.5 | 2.4 | 0.08 | 1.8 | 30 | 16 | 330 | 98.78 | 85.01 |
| Comparative Example 9 | 0.7 | 0.9 | 6.5 | 2.4 | 0.05 | 3.4 | 48 | 14 | 340 | 89.60 | 85.74 |
| Comparative Example 10 | 0.7 | 1.5 | 7.0 | 1.2 | 0.04 | 1.7 | 30 | 18 | 350 | 92.00 | 88.08 |
| Comparative Example 11 | 0.7 | 2.9 | 6.5 | 3.0 | 0.04 | 4.3 | 75 | 18 | 270 | 91.50 | 74.16 |
| Comparative Example 12 | 0.5 | 2.0 | 6.5 | 3.0 | 0.15 | 6.0 | 20 | 3 | 320 | 95.40 | 89.71 |
| Comparative Example 13 | 0.5 | 2.0 | 6.5 | 3.0 | 0.2 | 6.0 | 15 | 3 | 320 | 94.96 | 88.94 |
| Comparative Example 14 | 0.7 | 2.0 | 6.5 | 3.0 | 0.15 | 4.3 | 20 | 5 | 320 | 97.77 | 90.38 |
| Comparative Example 15 | 0.3 | 2.0 | 6.5 | 3.0 | 0.08 | 10.0 | 38 | 4 | 360 | 89.96 | 86.66 |
| Comparative Example 16 | 0.7 | 2.0 | 6.5 | 4.0 | 0.035 | 5.7 | 114 | 20 | 270 | 93.60 | 77.11 |
| Comparative Example 17 | 0.5 | 2.0 | 6.5 | 3.0 | 0.08 | 6.0 | 38 | 6 | 340 | 74.13 | 72.17 |

TABLE 1-continued

|  | a | b | c | d | g | d/a | d/g | a/g | Reaction bath temperature (° C.) | Propylene conversion (%) | Effective yield (%) |
|---|---|---|---|---|---|---|---|---|---|---|---|
| Comparative Example 18 | 0.5 | 2.0 | 6.5 | 3.0 | 0.08 | 6.0 | 38 | 6 | 350 | 83.74 | 81.05 |
| Comparative Example 19 | 0.5 | 2.0 | 6.5 | 3.0 | 0.08 | 6.0 | 38 | 6 | 340 | 83.90 | 81.20 |
| Comparative Example 20 | 0.4 | 2.0 | 6.5 | 2.0 | 0.01 | 5.0 | 200 | 40 | 310 | 95.60 | 87.80 |
| Comparative Example 21 | 0.9 | 2.0 | 8.2 | 2.4 | 0.04 | 2.7 | 60 | 21 | 260 | 78.14 | 64.93 |
| Comparative Example 22 | 0.7 | 2.0 | 4.0 | 3.0 | 0.04 | 4.3 | 75 | 18 | 320 | 94.33 | 89.13 |
| Comparative Example 23 | 0.7 | 2.0 | 8.0 | 3.0 | 0.04 | 4.3 | 75 | 18 | 329 | 85.03 | 52.98 |

When the conversion increases, the effective yield simultaneously increases, and therefore, the activity of the catalyst is compared in terms of the effective yield according to the conversion. The effective yield relative to the propylene conversion of each of the catalysts in the Examples and Comparative Examples is shown in FIG. 1. As a result of linking the plots in which a high effective yield relative to the propylene conversion is exhibited among the Comparative Examples, it was confirmed that all of the catalysts of the Examples with good performances exhibit a higher effective yield than the effective yield on this curve at the same propylene conversion and have a superior activity as compared with the Comparative Examples.

Figure 2:
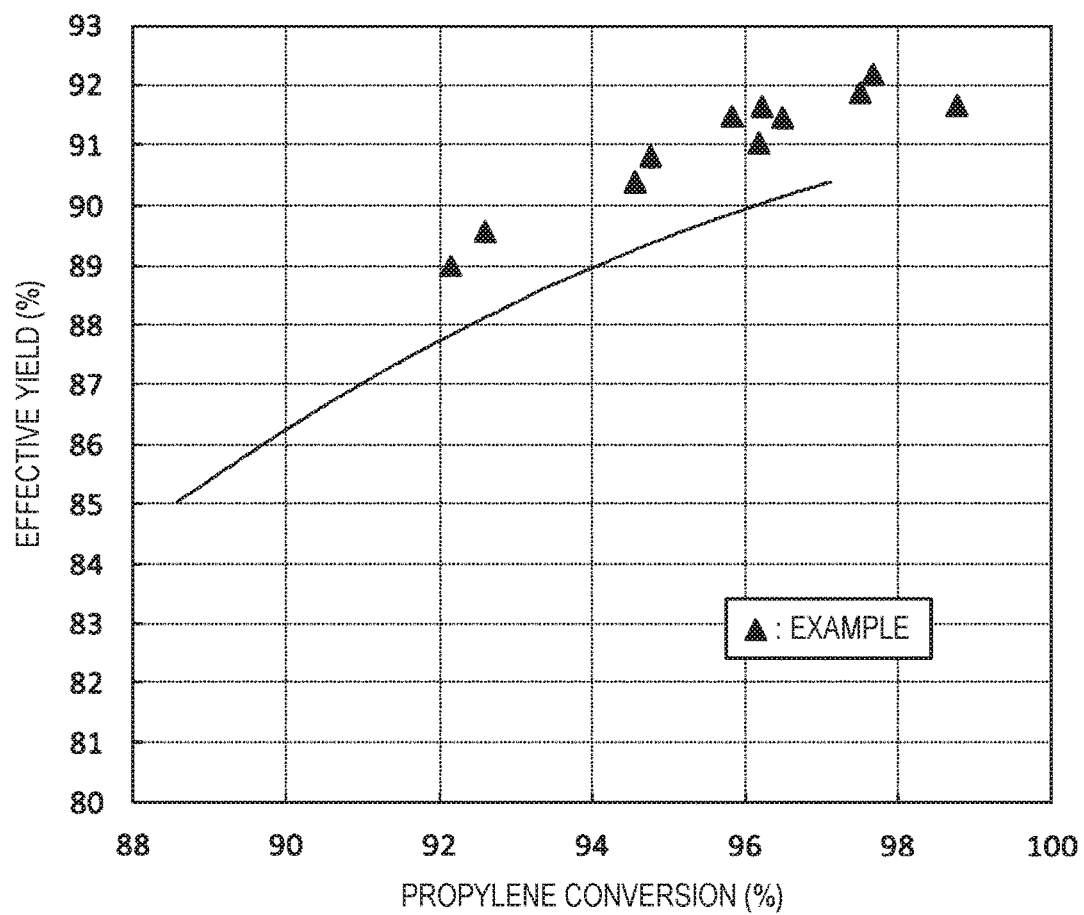
FIG. 2 is a graph showing a linear approximate curve of plots of an effective yield (%) relative to a propylene conversion (%) of each of catalysts in the Examples and an effective yield (%) relative to a propylene conversion (%) as evaluated by changing a calcination temperature and a reaction bath temperature in a catalyst having the same atomic ratio as in the catalyst of Comparative Example 1.

In addition, with respect to the catalysts composed of a composition of the same atomic ratios as the Spherical Catalyst 12 corresponding to Comparative Example 1, various evaluations were carried out in terms of the calcination temperature and the reaction bath temperature. A linear approximate curve of these plots of the effective yield relative to the propylene conversion was shown together with the Examples in FIG. 2. All of the catalysts of the Examples with good performances exhibited a higher effective yield than the effective yield on this curve at the same propylene conversion and had a superior activity. In other words, as for the catalysts falling outside the scope of the catalyst component of the present application, even by changing the calcination condition or the reaction bath temperature condition, a superior effective yield relative to the propylene conversion as in the catalyst of the present application was not revealed.

While the invention has been described in detail and with reference to specific embodiments thereof, it will be apparent to one skilled in the art that various changes and modifications can be made therein without departing from the spirit and scope thereof.

It is to be noted that the present application is based on a Japanese patent application filed on Feb. 27, 2015 (Japanese Patent Application No. 2015-037574), the entireties of which are incorporated by reference. In addition, all references cited herein are incorporated as a whole.

INDUSTRIAL APPLICABILITY

The catalyst of the present invention is useful for manufacturing of an unsaturated aldehyde and/or an unsaturated carboxylic acid.

The invention claimed is:

1. A method for manufacturing a compound corresponding to Formula (1):

$$Mo_{12}Bi_aFe_bCo_cNi_dZ_gO_h \quad \text{Formula (1)}$$

wherein
Z is one or more element(s) selected from the group consisting of sodium (Na), potassium (K), rubidium (Rb), and cesium (Cs); a to d and g and h represent atomic ratios of the respective components; h is a numerical value determined by oxidation degrees of the catalyst components; a is from 0.40 to 0.80; b is from 1.0 to 2.5; c is from 4.5 to 7.5; d is from 1.6 to 3.5; g is from 0.015 to 0.12; h is expressed by the numerical value satisfying the oxidation states of other elements; d/a is from 2.0 to 8.8; d/g is from 14 to 100; and a/g is from 3.5 to 53.3, the method comprising admixing:
i) a molybdenum component raw material comprising a molybdenum-containing compound, the molybdenum-containing compound being composed of only an ammonium molybdate, the ammonium molybdate being in an aqueous solution and the weight of water for dissolution being from 4.0 times to 8.5 times the weight of molybdenum contained in the ammonium molybdate; and
ii) a bismuth component raw material comprising a bismuth-containing compound, the bismuth-containing compound being composed of only bismuth nitrate, the bismuth nitrate being in an aqueous solution of nitric acid, the weight of a nitric acid aqueous solution for dissolution being 2.3 times or more the weight of bismuth contained in the bismuth nitrate, and the nitric acid concentration in the nitric acid aqueous solution for dissolving the bismuth nitrate is 10% by weight or more to obtain the compound corresponding to Formula (1).

2. The method according to claim 1, further comprising:
drying a slurry containing the compound corresponding to Formula (1) to obtain a dried slurry,
calcining the dried slurry at a temperature from 200° C. to 600° C. to obtain a first calcined powder,
admixing a binding agent to the first calcined powder to obtain an admixture of the first calcined powder, and
calcining the admixture of the first calcined powder at a temperature 200° C. to 600° C. to obtain a second calcined powder.

3. The method according to claim 1 further comprising coating a spherical carrier with the compound corresponding to Formula (1) to obtain a particle, the particle having an average particle diameter from 3.0 mm to 10 mm and the compound corresponding to Formula (1) comprising 20 wt % to 80 wt % of the spherical carrier.

* * * * *